(12) United States Patent
Lloyd et al.

(10) Patent No.: US 10,350,076 B2
(45) Date of Patent: Jul. 16, 2019

(54) CONVERTIBLE PRE-PARTIAL KNEE REPLACEMENT

(71) Applicant: Biomet Manufacturing, LLC, Warsaw, IN (US)

(72) Inventors: Russell Lloyd, Swindon (GB); Brian M. May, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/462,731

(22) Filed: Mar. 17, 2017

(65) Prior Publication Data
US 2017/0189192 A1 Jul. 6, 2017

Related U.S. Application Data

(62) Division of application No. 14/263,133, filed on Apr. 28, 2014, now Pat. No. 9,622,868.

(51) Int. Cl.
*A61F 2/38* (2006.01)
(52) U.S. Cl.
CPC .............. *A61F 2/3859* (2013.01); *A61F 2/38* (2013.01); *A61F 2/3836* (2013.01); *A61F 2/3868* (2013.01); *A61F 2002/3863* (2013.01); *A61F 2002/3895* (2013.01)
(58) Field of Classification Search
CPC ......... A61F 2/38; A61F 2/3836; A61F 2/3859
See application file for complete search history.

(56) References Cited

U.S. PATENT DOCUMENTS

| | | | |
|---|---|---|---|
| 3,715,763 | A | 2/1973 | Link |
| 4,085,466 | A | 4/1978 | Goodfellow et al. |
| 4,178,641 | A | 12/1979 | Grundei et al. |
| 5,021,061 | A | 6/1991 | Wevers et al. |
| 5,171,282 | A | 12/1992 | Pequignot |
| 6,383,222 | B1 | 5/2002 | Badorf |
| 6,554,866 | B1 | 4/2003 | Aicher et al. |
| 6,743,258 | B1 | 6/2004 | Keller |
| 7,758,652 | B2 | 7/2010 | Engh et al. |
| 8,246,687 | B2 | 8/2012 | Katrana et al. |

(Continued)

FOREIGN PATENT DOCUMENTS

| | | |
|---|---|---|
| CN | 2350012 Y | 11/1999 |
| CN | 106535828 A | 3/2017 |

(Continued)

OTHER PUBLICATIONS

"U.S. Appl. No. 14/263,133, Advisory Action dated Jun. 22, 2016", 2 pgs.

(Continued)

*Primary Examiner* — Bruce E Snow
(74) *Attorney, Agent, or Firm* — Schwegman Lundberg & Woessner, P.A.

(57) ABSTRACT

A unicondylar resurfacing femoral component including a metallic base member and a polymeric articulation member. The metallic base member includes a main body and a retention member extending from the main body configured to be secured within a condyle of a femur. The polymeric articulation member is coupled to the main body of the metallic base member and includes an articulation surface configured to articulate directly against a planar surface of a metallic tibial component.

10 Claims, 4 Drawing Sheets

(56) References Cited

U.S. PATENT DOCUMENTS

| | | | |
|---|---|---|---|
| 9,216,085 B2* | 12/2015 | Schwartz | A61F 2/30756 |
| 9,622,868 B2 | 4/2017 | Lloyd et al. | |
| 2001/0016778 A1 | 8/2001 | Badorf et al. | |
| 2004/0054417 A1 | 3/2004 | Soffiati et al. | |
| 2005/0283253 A1 | 12/2005 | Coon et al. | |
| 2006/0004460 A1 | 1/2006 | Engh et al. | |
| 2006/0235537 A1 | 10/2006 | Kuczynski et al. | |
| 2007/0100460 A1 | 5/2007 | Rhodes | |
| 2007/0233266 A1 | 10/2007 | Williams, III et al. | |
| 2008/0215157 A1 | 9/2008 | Earl et al. | |
| 2009/0125115 A1 | 5/2009 | Popoola et al. | |
| 2009/0248166 A1 | 10/2009 | Linares | |
| 2011/0178607 A1* | 7/2011 | Oosthuizen | A61F 2/38 623/20.35 |
| 2012/0116524 A1 | 5/2012 | Walker et al. | |
| 2013/0060344 A1 | 3/2013 | Pierce | |
| 2013/0166037 A1 | 6/2013 | Goodfellow et al. | |
| 2014/0067079 A1* | 3/2014 | Walker | A61F 2/3859 623/20.35 |
| 2015/0305874 A1 | 10/2015 | Lloyd et al. | |

FOREIGN PATENT DOCUMENTS

| | | | |
|---|---|---|---|
| FR | 2851156 A1 | 8/2004 | |
| FR | 2851156 B1 | 4/2005 | |
| JP | 2017513647 A | 6/2017 | |
| WO | 2004078074 | 9/2004 | |
| WO | WO-2015167985 A1 | 11/2015 | |

OTHER PUBLICATIONS

"U.S. Appl. No. 14/263,133, Advisory Action dated Nov. 14, 2016", 2 pgs.
"U.S. Appl. No. 14/263,133, Final Office Action dated Apr. 15, 2016", 9 pgs.
"U.S. Appl. No. 14/263,133, Final Office Action dated Sep. 1, 2016", 11 pgs.
"U.S. Appl. No. 14/263,133, Non Final Office Action dated Dec. 11, 2015", 10 pgs.
"U.S. Appl. No. 14/263,133, Notice of Allowance dated Dec. 12, 2016", 5 pgs.
"U.S. Appl. No. 14/263,133, Response filed Mar. 11, 2016 to Non Final Office Action dated Dec. 11, 2015", 6 pgs.
"U.S. Appl. No. 14/263,133, Response filed Jun. 15, 2016 to Final Office Action dated Apr. 15, 2016", 6 pgs.
"U.S. Appl. No. 14/263,133, Response filed Oct. 31, 2016 to Final Office Action dated Sep. 1, 2016", 6 pgs.
"U.S. Appl. No. 14/263,133, Response filed Nov. 18, 2015 to Restriction Requirement dated Sep. 18, 2015", 5 pgs.
"U.S. Appl. No. 14/263,133, Restriction Requirement dated Sep. 18, 2015", 7 pgs.
"International Application Serial No. PCT/US2015/027717, International Preliminary Report on Patentability dated Nov. 10, 2016", 10 pgs.
"International Application Serial No. PCT/US2015/027717, International Search Report dated Jul. 3, 2015", 6 pgs.
"International Application Serial No. PCT/US2015/027717, Written Opinion dated Jul. 3, 2015", 9 pgs.
"European Application Serial No. 15721477.6, Response filed Jun. 29, 2017 to Communication pursuant to Rules 161(1) and 162 EPC dated Dec. 21, 2016", 10 pgs.
"Chinese Application Serial No. 201580029100.X, Office Action dated Sep. 19, 2017", (W/ English Translation), 19 pgs.
"Chinese Application Serial No. 201580029100.X, Response filed Jan. 22, 2018 to Office Action dated Sep. 19, 2017", (W/ English Translation of Claims), 11 pgs.
"Chinese Application Serial No. 201580029100.X, Office Action dated Apr. 18, 2018", W/ English translation), 20 pgs.
"Chinese Application Serial No. 201580029100.X, Response filed Jul. 3, 2018 to Office Action dated Apr. 18, 2018", (W/ English Translation of Claims), 10 pgs.
"Japanese Application Serial No. 2016-565004, Notification of Reasons for Refusal dated Jan. 8, 2019", w English translation, 12 pgs.

* cited by examiner

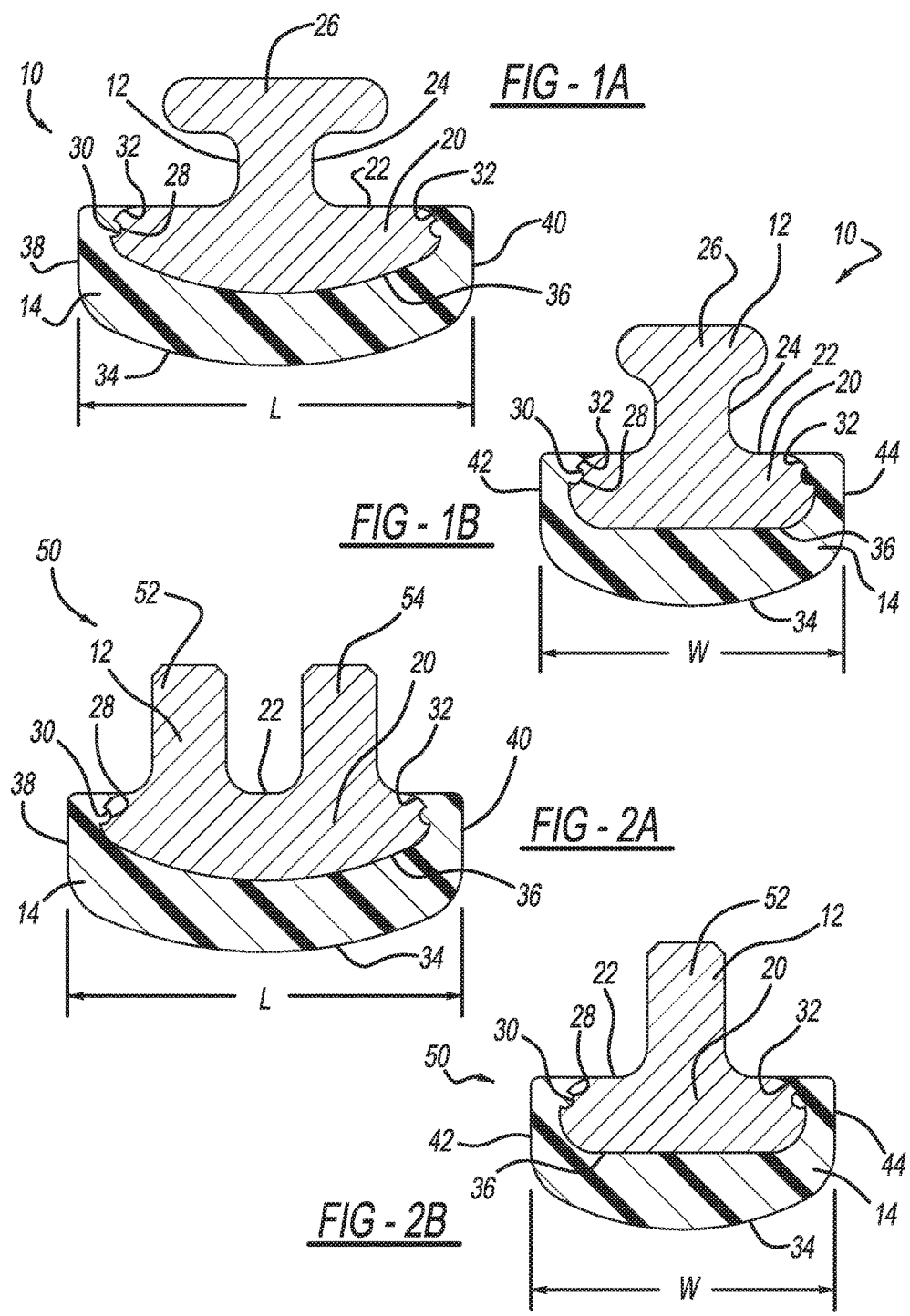

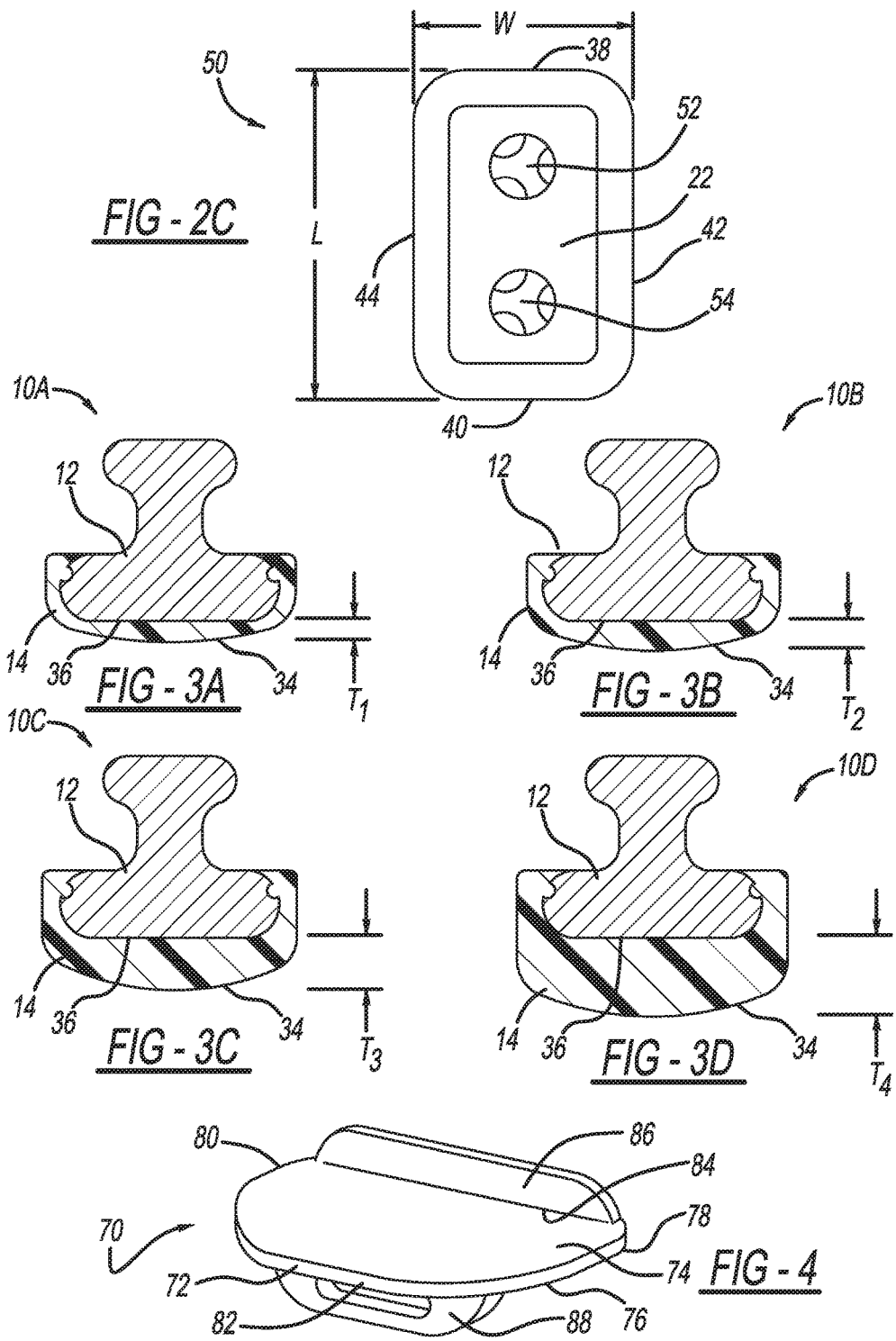

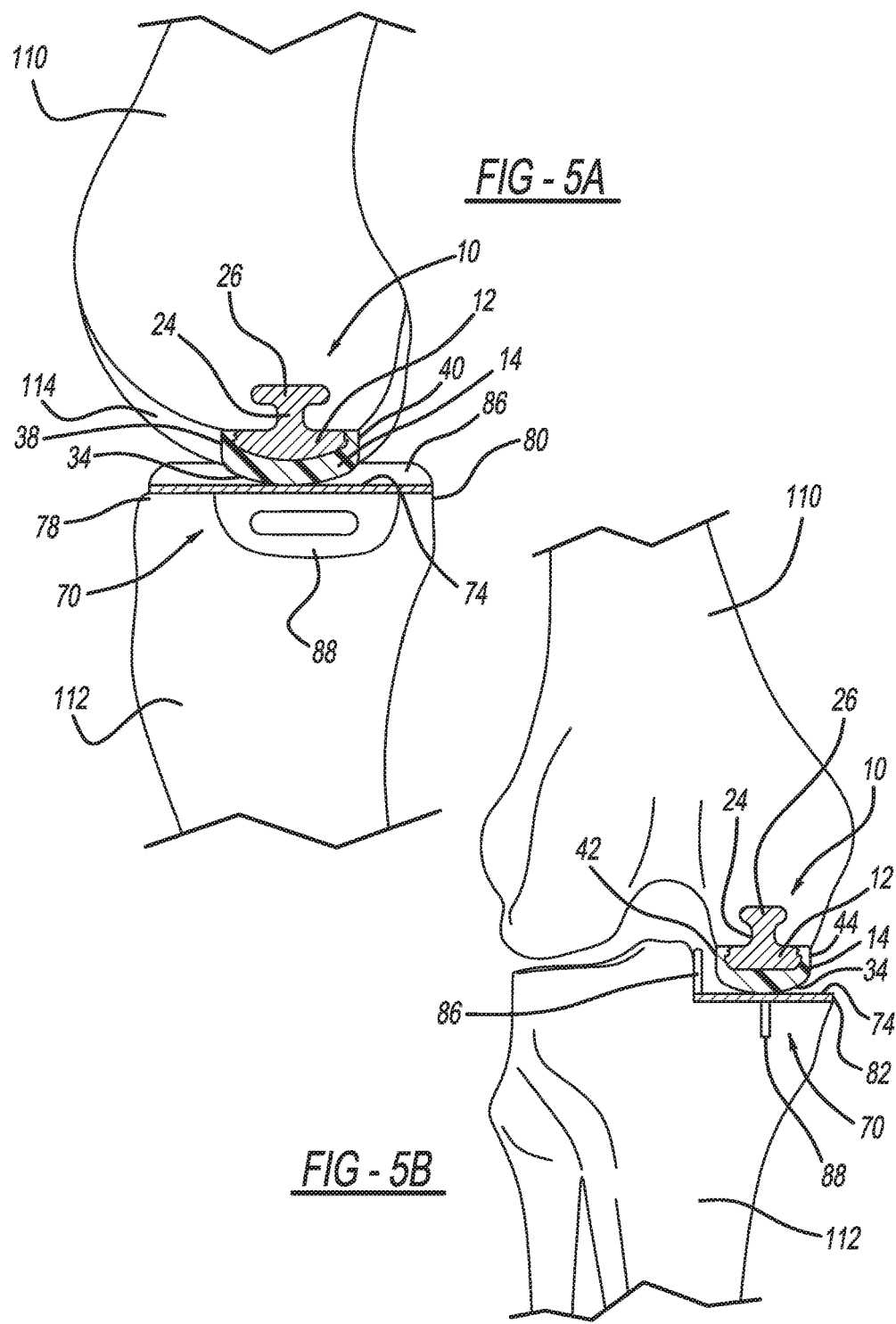

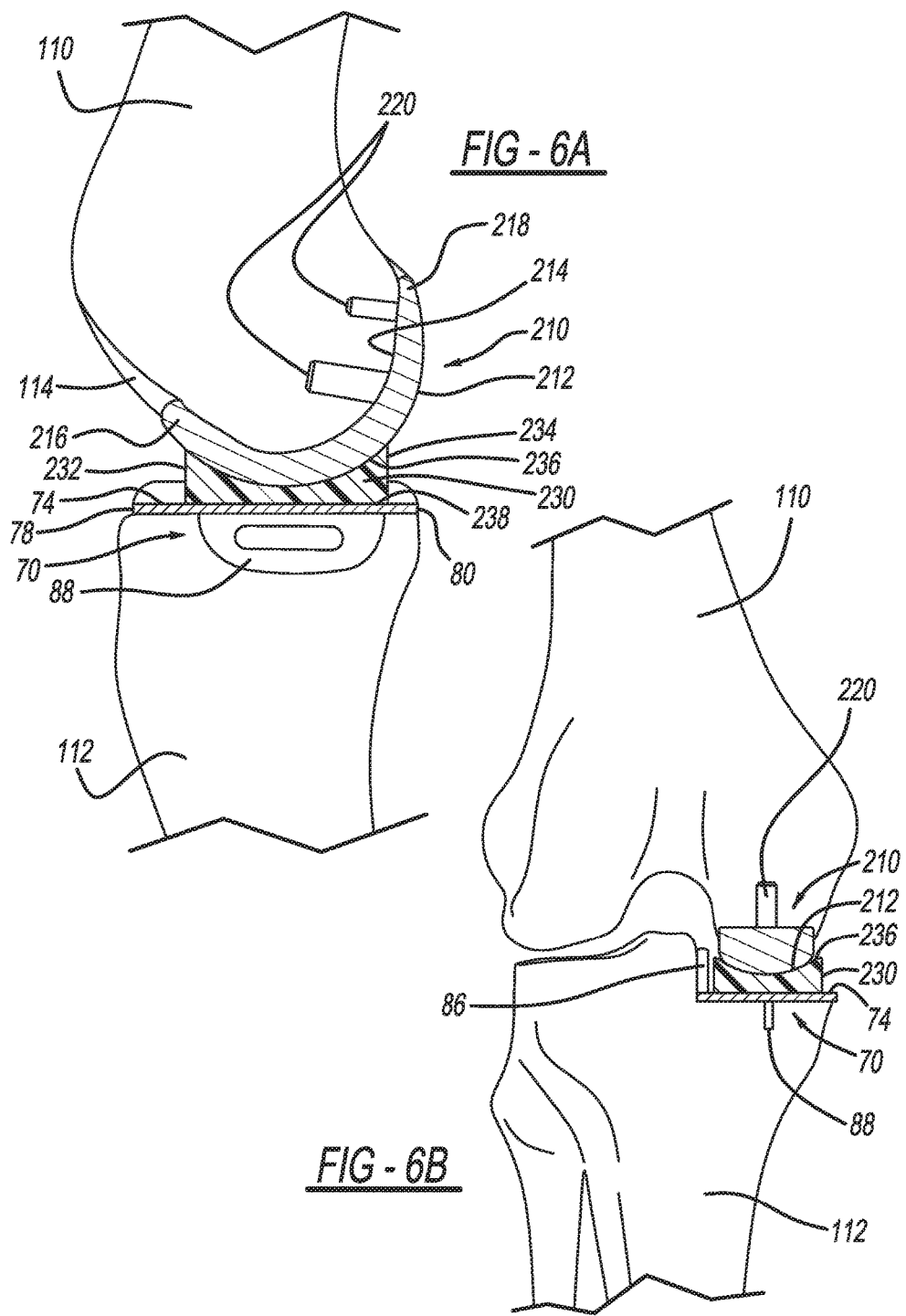

CONVERTIBLE PRE-PARTIAL KNEE REPLACEMENT

FIELD

The present disclosure relates to a convertible pre-partial knee replacement assembly.

BACKGROUND

This section provides background information related to the present disclosure, which is not necessarily prior art.

Femoral condyles of the knee joint may require repair or replacement for a variety of different reasons, such as due to bone degradation or a focal defect. Osteoarthritis is a relatively common condition that results in bone degradation. A unicondylar resurfacing femoral implant would be desirable to address these conditions. Because these conditions may worsen with time, it may be necessary to replace the resurfacing implant with a full unicondylar implant, such as the Oxford® Partial Knee by Biomet of Warsaw, Ind. Both the resurfacing implant and full unicondylar implant typically articulate with a tibial implant. A unicondylar resurfacing implant that can articulate with a tibial implant of a full unicondylar implant, such as the Oxford® tibial implant, would therefore be desirable because such a resurfacing implant would eliminate the need to revise the tibia, which will advantageously conserve bone. The present teachings provide for unicondylar resurfacing femoral components, assemblies, and methods that address these issues and needs, among others.

SUMMARY

This section provides a general summary of the disclosure, and is not a comprehensive disclosure of its full scope or all of its features.

The present teachings provide for a unicondylar resurfacing femoral component including a metallic base member and a polymeric articulation member. The metallic base member includes a main body and a retention member extending from the main body configured to be secured within a condyle of a femur. The polymeric articulation member is coupled to the main body of the metallic base member and includes an articulation surface configured to articulate directly against a planar surface of a metallic tibial component.

The present teachings further provide for a unicondylar resurfacing femoral assembly including a unicondylar resurfacing femoral component and a tibial component. The unicondylar resurfacing femoral component includes a metallic base member and a polymeric articulation member. The tibial component includes a tibial tray with a planar, superior articulating surface and a tibial retention member extending from an inferior surface of the tibial tray. The planar, superior articulating surface of the tibial component is configured to directly articulate with the polymeric articulation member. The planar, superior articulating surface of the tibial component is further configured to articulate with, by way of a slidable bearing seated on the superior articulating surface, a revision femoral component implanted in a femur in place of the unicondylar resurfacing femoral component after the unicondylar resurfacing femoral component has been removed from the femur.

The present teachings still further provide for a method for repairing a defect in a femur at a condyle thereof. The method includes the following: cutting the condyle at the defect to form an implant site; implanting a unicondylar resurfacing femoral component at the implant site in the condyle such that a metallic base member is secured within the condyle and a polymeric articulation member extends into a joint space defined between the femur and a tibia; preparing the tibia to receive a tibial component; and implanting the tibial component into the tibia, the tibial component including a planar, superior articulating surface. The polymeric articulation member has a thickness sufficient to extend to, and directly articulate with, the superior articulating surface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1A is a cross-sectional view of a unicondylar resurfacing femoral component according to the present teachings taken in an anterior-posterior direction;

FIG. 1B is a cross-sectional view of the femoral component of FIG. 1A taken in a medial-lateral direction;

FIG. 2A is a cross-sectional view of another unicondylar resurfacing femoral component according to the present teachings taken in the anterior-posterior direction;

FIG. 2B is a cross-sectional view of the femoral component of FIG. 2A taken in the medial-lateral direction;

FIG. 2C is a planar view of a superior surface of the femoral component of FIG. 2A;

FIG. 3A is a medial-lateral cross-sectional view of the femoral component of FIGS. 1A and 1B including an articulation member with a first thickness;

FIG. 3B is a medial-lateral cross-sectional view of the femoral component of FIGS. 1A and 1B including an articulation member with a second thickness;

FIG. 3C is a medial-lateral cross-sectional view of the femoral component of FIGS. 1A and 1B including an articulation member with a third thickness;

FIG. 3D is a medial-lateral cross-sectional view of the femoral component of FIGS. 1A and 1B including an articulation member with a fourth thickness;

FIG. 4 is a perspective view of a tibial component according to the present teachings;

FIG. 5A is a cross-sectional view taken in an anterior-posterior direction illustrating the femoral component of FIGS. 1A and 1B implanted in a femur and the tibial component of FIG. 4 implanted in a tibia;

FIG. 5B is a cross-sectional view taken in the medial-lateral direction of the femoral component of FIGS. 1A and 1B implanted in the femur and the tibial component of FIG. 4 implanted in the tibia;

FIG. 6A is a cross-sectional view taken in the anterior-posterior direction of a revision femoral component according to the present teachings implanted in the femur for articulation with the tibial component of FIGS. 4, 5A, and 5B by way of a bearing; and FIG. 6B is a cross-sectional view taken in the medial-lateral direction of the revision femoral component of FIG. 6A implanted in the femur for articulation with the tibial component of FIGS. 4, 5A, and 5B by way of a bearing.

DETAILED DESCRIPTION

Example embodiments will now be described more fully with reference to the accompanying drawings.

With initial reference to FIGS. 1A and 1B, a unicondylar resurfacing femoral component according to the present teachings is illustrated at reference numeral 10. The femoral component 10 generally includes a base member 12 and an articulation member 14. The base member 12 can be made of any suitable biocompatible material, such as any suitable metallic material including cobalt-chrome, for example. The articulation member 14 can be made of any suitable biocompatible material, such as a non-metallic material including ultrahigh molecular weight polyethylene (UHMWPE).

The base member 12 generally includes a main body 20 having a superior body surface 22. Extending from the superior body surface 22 is any suitable retention member configured for anchoring the femoral component 10 in a femur. For example and as illustrated in FIGS. 1A and 1B, the retention member may include a neck 24 extending to a flange 26. The flange 26 can be oriented such that it extends in a direction generally transverse to a direction that the neck 24 extends from the main body 20. For example, the flange can extend generally in an anterior-posterior direction. In place of or in addition to including the neck 24 and the flange 26, the retention member can have any suitable configuration sufficient to anchor the femoral component 10 in a femur. For example, the retention member may be and/or include a post, peg, or keel. The retention member can be secured within the femur in any suitable manner, such as with bone cement or a press-fit.

The main body 20 defines a recess or undercut 28 generally extending about an outer periphery 32 thereof proximate to the superior body surface 22. The recess or undercut 28 is sized and shaped in any suitable manner to cooperate with a corresponding member or portion of the articulation member 14. For example, the recess or undercut 28 can be sized and shaped to receive a protrusion 30 of the articulation member 14. As illustrated in FIGS. 1A and 1B, for example, the protrusion 30 extends inward to sit within the recess 28 to couple the articulation member 14 to the main body 20. To further secure the articulation member 14 to the main body 20, the articulation member 14 is arranged such that it extends beyond the recess 28 and over the outer periphery 32 towards the superior body surface 22, such that the articulation member 14 generally hooks over the outer periphery 32 of the main body 20.

The articulation member 14 includes an articulation surface 34 and an inner surface 36 generally opposite thereto. The inner surface 36 abuts the main body 20. The articulation surface 34 extends between an anterior end 38 and a posterior end 40 of the femoral component 10 in a curved manner such that the articulation surface 34 has a concave shape. A length L of the femoral component 10 is defined between the anterior end 38 and the posterior end 40. With reference to FIG. 1B, the articulation surface 34 also extends between a medial side 42 and a lateral side 44 of the femoral component 10 in a curved manner such that the articulation surface 34 has a concave shape. A width W of the femoral component 10 is defined between the medial side 42 and the lateral side 44.

With additional reference to FIGS. 2A-2C, an additional femoral component according to the present teachings is generally illustrated at reference numeral 50. Like the femoral component 10, the femoral component 50 is a unicondylar resurfacing femoral component. The femoral component 50 is similar to the femoral component 10, and thus similar features are designated in the Figures with like reference numerals, and the description of the like features set forth above in the description of femoral component 10 also describes the femoral component 50.

The femoral retention member of the femoral component 50 differs from that of the femoral component 10. Specifically, the femoral component 50 includes a femoral retention member in the form of a first or anterior post 52 and a second or posterior post 54 spaced apart from the first or anterior post 52. The anterior post 52 is proximate to the anterior end 38, and the posterior post 54 is proximate to the posterior end 40. The posts 52 and 54 can be of any suitable length to secure the femoral component 50 within a femur. The femoral component 50 can be secured within the femur in any suitable manner, such as with bone cement or a press-fit.

With additional reference to FIGS. 3A-3C, the articulation member 14 can be provided with different thicknesses $T_1$-$T_4$. Although FIGS. 3A-3D illustrate the articulation member 14 in conjunction with the femoral component 10, the articulation member 14 of the femoral component 50 may include thicknesses $T_1$-$T_4$ as well. In addition to the thicknesses $T_1$-$T_4$, any suitable thickness of the articulation member 14 can be provided. The femoral component 10, as well as the femoral component 50, can be provided as part of a kit of multiple femoral components 10 or 50, one or more of which include different thicknesses of the articulation member 14, such as the thicknesses $T_1$-$T_4$, or any other suitable thickness.

The thickness T is generally measured as a distance between the articulation surface 34 and the inner surface 36 opposite thereto. FIGS. 3A-3D illustrate the thickness T with respect to the thicknesses $T_1$-$T_4$, as being measured between a most inferior portion of the inner surface 36 and a most inferior portion of the articulation surface 34. However, the thickness T may be measured between any portion of the articulation surface 34 and the inner surface 36 opposite thereto. Any suitable thickness T, such as $T_1$-$T_4$, can be selected for implantation. For example, a thickness T sufficient to span a joint space between a femur 110 and a tibia 112 to mate with a tibial component 70 (see FIGS. 5A, 5B, 6A, and 6B) can be selected. In some applications, the thickness T can be similar to a thickness of cartilage 114 (FIG. 5A for example).

With additional reference to FIG. 4, a tibial component according to the present teachings is generally illustrated at reference numeral 70. The tibial component 70 generally includes a tibial tray or base 72, having a superior articulation surface 74 and an inferior surface 76 opposite thereto. The superior articulation surface 74 is generally a planar articulation surface against which the articulation surface 34 of the articulating member 14 can articulate.

The tibial tray or base 72 further includes an anterior end 78, a posterior end 80, a lateral end or side 82, and a medial end or side 84. Extending superiorly at the medial end 84 generally between the anterior and posterior ends 78 and 80 is a sidewall 86. A tibial retention member or flange 88 extends from the inferior surface 76. The tibial retention member 88 can be any suitable member configured to anchor the tibial component 70 within a tibia. For example and as illustrated, the tibial retention member 88 can generally be an elongated flange extending in an anterior-posterior direction.

With additional reference to FIGS. 5A and 5B, the femoral component 10 and the tibial component 70 are illustrated implanted within the femur 110 and the tibia 112 respectively in order to provide a condylar resurfacing assembly. As illustrated in FIG. 5A, for example, the femoral component 10 extends only a relatively short distance in the anterior-posterior direction, as compared to a traditional uni-condylar implant, which typically wraps around the condyle further in both the anterior and posterior direction (similar to the revision femoral component 210 described herein and illustrated in FIGS. 6A and 6B). Unlike traditional uni-condylar femoral components, the femoral component 10 according to the present teachings is specifically configured to address relatively small femoral defects (smaller than would typically be treated with a traditional uni-condylar implant, such as the revision femoral component 210), such as those caused by osteoarthritis or focal defects, and to articulate directly with the tibial component 70 without a separate bearing therebetween. As described herein, the tibial component 70 is configured to individually articulate with the femoral component 10 or 50 directly, and with the revision femoral component 210 by way of bearing 230 subsequent to replacement of the femoral component 10 or 50 with the revision femoral component 210.

A method of implanting the femoral component 10 and the tibial component 70 will now be described. After the femoral and/or tibial defect is detected, such as an osteoarthritis and/or focal defect, the defect can be removed in any suitable manner. For example, the femoral defect can be removed using any suitable device, such as a burr, punch, rasp, drill or pick device used during mosaicplasty. An opposing tibial resection can be made in any suitable manner, such as with a tibial saw, to form a planar tibial plateau. The tibial resection can be made to accommodate a full unicondylar femoral component, such as the Oxford® Partial Knee implant by Biomet of Warsaw, Ind., which is similar to, and can be the same as, the revision femoral component 210.

After the femur 110 and the tibia 112 have been prepared, trials of the femoral component 10 are inserted where the femur 110 has been cut to determine the appropriate thickness T of the articulation member 14. The appropriate thickness T will generally be a thickness T sufficient to extend across the joint space defined between the femur 110 and the tibia 112 in order to contact and articulate with the superior articulation surface 74 of the tibial component 70. After the femoral component 10 having the articulation member 14 with the appropriate thickness T is identified, such as any one of femoral components 10A-10D having thicknesses $T_1$-$T_4$, the femoral component 10 is implanted in the femur 110 by inserting the flange 26 of the base member 12 within the cut area of the femur 110, and securing the flange 26 therein in any suitable manner, such as with bone cement or a press-fit. The femoral component 50 can be implanted in generally the same manner as described above with respect to the femoral component 10. The tibial component 70 is seated on the prepared tibial surface and the tibial retention member 88 is secured therein in any suitable manner, such as with bone cement or a press fit. The articulation surface 34 of the femoral component 10 or 50 contacts and articulates directly with the superior articulation surface 74 of the tibial component 70 to permit articulation between the femur 110 and the tibia 112.

In some cases, such as if a patient's osteoarthritis worsens for example, the femoral component 10 or 50 may need to be replaced with a full unicondylar femoral component, such as with the revision femoral component 210 of FIGS. 6A and 6B. Any suitable full unicondylar femoral component can be used as the revision femoral component 210, such as that of the Oxford® Partial Knee implant by Biomet of Warsaw, Ind. The revision femoral component 210 can be made of any suitable material, such as any suitable hard material. For example, the revision femoral component 210 can be made of a suitable metallic material including CoCr.

The revision femoral component 210 generally includes an articulation surface 212 and a bone engaging surface 214 opposite thereto. Each one of the articulation surface 212 and the bone engaging surface 214 generally extend between an anterior end 216 and a posterior end 218 of the femoral component 210. The distance between the anterior end 216 and the posterior end 218 of the revision femoral component 210 is substantially greater than the length L of the femoral component 10 between the anterior end 38 and the posterior end 40. The revision femoral component 210 may also have a medial-lateral width that is equal to or greater than the width W of the femoral component 10 between the medial and lateral sides 42 and 44. Extending from the bone engaging surface 214 is one or more fixation members 220, such as posts as illustrated. Upon removal of the femoral component 10 bone holes for the fixation members 220 can be formed in any suitable manner and the fixation members 220 can be secured therein with bone cement or press-fit, for example.

The revision femoral component 210 is configured to articulate with bearing 230, which can be a mobile bearing. The bearing 230 can be made of any suitable material, such as any suitable polymeric material including ultrahigh molecular weight polyethylene (UHMWPE). The bearing 230 generally includes an anterior end 232 and a posterior end 234. Between the anterior and posterior ends 232 and 234 is an articulation surface 236 and a planar surface 238 opposite to the articulation surface 236. The bearing 230 is seated on the tibial component 70 such that that the planar surface 238 slidably cooperates with the superior articulation surface 74. The articulation surface 212 of the revision femoral component 210 is mated with the articulation surface 236 of the bearing 230 to permit articulation between the revision femoral component 210 and the tibial component 70 by way of the bearing 230. Because the same tibial component 70 can articulate with the revision femoral component 210, the tibia 112 does not have to be revised when the revision femoral component 210 is implanted, which advantageously conserves bone.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for repairing a defect in a femur at a condyle thereof comprising:
cutting the condyle at the defect to form an implant site;
selecting a unicondylar resurfacing femoral component from a plurality of different unicondylar resurfacing femoral components having polymeric articulation members of different thicknesses;
implanting the unicondylar resurfacing femoral component at the implant site in the condyle such that a metallic base member is secured within the condyle and the polymeric articulation member extends into a joint space defined between the femur and a tibia;

preparing the tibia to receive a tibial component; and implanting the tibial component into the tibia, the tibial component including a planar, superior articulating surface; and trialing the selected polymeric articulation member, wherein when trialing the polymeric articulation member the selected polymeric articulation member has a thickness sufficient to span the joint space between the femur and the tibial component such that the polymeric articulation member extends to and directly articulates with the superior articulating surface.

2. The method of claim 1, further comprising:

replacing the implanted unicondylar resurfacing femoral component with a revision femoral component having a first anterior-posterior length that is greater than a second anterior-posterior length of the unicondylar resurfacing femoral component;

arranging a polymeric bearing on the superior articulating surface of the tibial component such that the polymeric bearing is configured to slide along the superior articulating surface; and mating the revision femoral component with the polymeric bearing to permit articulation between the revision femoral component and the tibial component indirectly by way of the bearing.

3. The method of claim 2, wherein the tibial component and the tibia are not revised to accommodate the revision femoral component.

4. The method of claim 1, wherein the tibial component includes a tibial tray with the planar, superior articulating surface and a tibial retention member extending from an inferior surface of the tibial tray.

5. The method of claim 1, further comprising:

replacing the implanted unicondylar resurfacing femoral component with a revision femoral component having a first anterior-posterior length that is greater than a second anterior-posterior length of the unicondylar resurfacing femoral component;

arranging a slidable bearing on the superior articulating surface of the tibial component such that the slidable bearing is configured to slide along the superior articulating surface; and mating the revision femoral component with the slidable bearing to permit articulation between the revision femoral component and the tibial component indirectly by way of the bearing.

6. The method of claim 1, wherein the metallic base member includes a main body and a retention member extending from the main body configured to be secured within a condyle of the femur.

7. The method of claim 6, wherein the retention member is one of a post, flange, peg, or keel.

8. The method of claim 6, wherein the retention member includes an anterior post and a posterior post spaced apart from the anterior post.

9. The method of claim 1, wherein the metallic base member includes a main body and wherein the main body defines a recess configured to cooperate with a protrusion of the polymeric articulation member to secure the polymeric articulation member to the main body.

10. The method of claim 1, wherein the tibial component includes a tibial tray having the planar, superior articulating surface, a retention flange extending from an inferior surface of the tibial tray, and a sidewall extending superiorly at a medial end of the tibial tray.

* * * * *

UNITED STATES PATENT AND TRADEMARK OFFICE
CERTIFICATE OF CORRECTION

PATENT NO. : 10,350,076 B2  Page 1 of 1
APPLICATION NO. : 15/462731
DATED : July 16, 2019
INVENTOR(S) : Lloyd et al.

It is certified that error appears in the above-identified patent and that said Letters Patent is hereby corrected as shown below:

On the Title Page

In item (72), in "Inventors", in Column 1, Line 1, after "Swindon", insert --Wiltshire--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*